United States Patent
Pechstein et al.

(10) Patent No.: US 7,704,357 B2
(45) Date of Patent: Apr. 27, 2010

(54) POTENTIOMETRIC SENSOR

(75) Inventors: Torsten Pechstein, Radebeul (DE); Detlev Wittmer, Maulbronn (DE); Hermann Straub, Rottenburg (DE); Dirk Steinmueller, Karlsruhe (DE)

(73) Assignee: Endress + Hauser Conducta Gesellschaft fur Mess- und Regeltechnik MBh + Co. KG, Gerlingen (DE)

(*) Notice: Subject to any disclaimer, the term of this patent is extended or adjusted under 35 U.S.C. 154(b) by 806 days.

(21) Appl. No.: 10/530,344

(22) PCT Filed: May 15, 2003

(86) PCT No.: PCT/EP03/05108

§ 371 (c)(1),
(2), (4) Date: Nov. 21, 2006

(87) PCT Pub. No.: WO2004/102175

PCT Pub. Date: Nov. 25, 2004

(65) Prior Publication Data

US 2007/0110620 A1    May 17, 2007

(51) Int. Cl.
*G01N 27/26* (2006.01)

(52) U.S. Cl. ............ 204/406; 204/403.1; 204/407; 204/408; 204/416; 204/433; 204/435

(58) Field of Classification Search ........... 204/403.01, 204/406, 407, 408, 416, 433, 435
See application file for complete search history.

(56) References Cited

U.S. PATENT DOCUMENTS

| 4,157,283 | A | * | 6/1979 | Zetter ............ 205/786.5 |
| 4,858,615 | A | * | 8/1989 | Meinema .......... 600/481 |
| 5,357,953 | A | | 10/1994 | Merrick |
| 5,366,609 | A | | 11/1994 | White |
| 5,384,028 | A | | 1/1995 | Ito |
| 5,425,361 | A | | 6/1995 | Fenzlein |
| 5,690,893 | A | | 11/1997 | Ozawa et al. |
| 5,711,861 | A | | 1/1998 | Ward |
| 6,053,031 | A | | 4/2000 | Kullik |
| 2002/0070128 | A1 | | 6/2002 | Beckmann |

FOREIGN PATENT DOCUMENTS

| DE | 4 139 122 | 4/1993 |
| DE | 1 972 2744 | 12/1998 |
| DE | 10062062 | 2/2002 |
| EP | 0 548 751 A1 | 6/1993 |
| EP | 054 8751 | 6/1993 |
| EP | 0 571 225 A2 | 11/1993 |
| EP | 1 143239 A1 | 10/2001 |
| JP | 10-253572 | 9/1998 |
| WO | WO 92/17775 | 10/1992 |

* cited by examiner

*Primary Examiner*—Bruce F Bell
(74) *Attorney, Agent, or Firm*—Bacon & Thomas, PLLC

(57) ABSTRACT

A potentiometric sensor, especially a pH-sensor or redox-sensor, includes: an elementary sensor for registering a potentiometric parameter, especially a pH-value or a redox potential; and an interface for issuing a potentiometric-parameter-dependent signal to a superordinated unit, especially a transmitter; wherein the potentiometric sensor of the invention has a digital data memory, which is permanently connected with elementary sensor.

7 Claims, 1 Drawing Sheet

POTENTIOMETRIC SENSOR

FIELD OF THE INVENTION

The present invention relates to potentiometric sensors, particularly a pH-sensor or a redox-sensor, respectively a pH-electrode or a redox-electrode, for connection to a transmitter.

BACKGROUND OF THE INVENTION

Potentiometric sensors measure potentials where resistances are large, as is the case with pH-sensors and redox-sensors. PH-electrodes, respectively redox-electrodes, register particularly ionic potentials in solutions. In many applications, they are exposed to heavy wear, such that they are often replaced after short operating times. In this respect, these electrodes are consumable materials, which are to be provided as cost-effectively as possible with given precision of measurement.

The present invention will be explained on the basis of examples of pH-electrodes, respectively pH-sensors. However, the embodiments logically apply to other potentiometric sensors as well, particularly redox-sensors, respectively redox-electrodes.

Essentially three types of pH-sensors are known in the state of the art, and these will now be outlined briefly.

The simplest pH-sensors are simple pH-electrodes without any electronics. These pH-electrodes deliver a pH-dependent potential, which can be accessed at suitable electrical connections. Optionally, these pH-electrodes have an integrated temperature sensor for temperature compensation, e.g. PT100, the potential of which can be measured at suitable temperature outputs. For measuring, these pH-sensors are normally connected by means of a cable to a transmitter, which generates a measuring signal from the pH-dependent potential and, if necessary, from the temperature signal of the temperature sensor.

In addition to the described, simple pH-electrodes, respectively sensors, described, there are such with an integrated preamplifier for impedance conversion. The output signal of the preamplifier is the potential of the pH-sensor, with the internal resistance of the preamplifier amounting to only a few ohms, instead of the internal resistance of the pH-sensor in the order of magnitude of 100 megohms. Thus, the further transfer to, and processing of the output potential for, a transmitter is greatly simplified. The preamplifiers are either battery-powered, or are fed by means of a cable.

Finally, simple transmitters, which are mounted directly on the pH-sensor, are available under the name "DirectLine" from Honeywell. Consequently, in the direct vicinity of the sensor, e.g. a 4-20 mA measurement signal is generated, which can then be transferred without further ado to a control room.

For all pH-electrodes, respectively pH-sensors of the state of the art, it is necessary to calibrate the electrodes after the connection to the transmitter, whereupon the acquired calibration parameters are stored in the transmitter. Although this way of doing things enables, in most cases, satisfactory measuring operation following the calibration, it does have, however, several serious disadvantages.

Sensors must be recalibrated when they are connected to another transmitter. Sensors without prior calibration are not operable.

Sensor-specific additional information, such as type designation, service life, or historical data, is not available for every sensor, or is available only with great effort, especially when the affiliation a sensor and a transmitter has been lost.

Sensors must normally be calibrated at the site of the transmitter. Particularly in cases where adverse working conditions prevail at the site of transmitter, complex calibrations, such as the identification of the isothermal working point, are practically impossible to perform. This leads to compromises with respect to the achievable precision of measurement.

SUMMARY OF THE INVENTION

An object of the present invention is to provide a pH-sensor which overcomes the described disadvantages of the state of the art.

This object is achieved by the pH-sensor including: an elementary sensor for registering a pH-value; a digital data memory permanently connected with the elementary sensor for storing sensor data or process data; and an interface for connection to a superordinated unit for transferring a signal representing the pH-value, and for reading and/or writing digital data from, respectively to, the digital data memory.

The digital data memory is permanently connected with the elementary sensor in so far as the data memory and the elementary sensor form an inseparable unit.

The superordinated unit is especially a transmitter or another suitable device for registering and processing the data of the pH-sensor.

Fundamentally, it is unimportant for the invention whether the analog electronics necessary for the operation of the sensor is likewise permanently connected with the pH-sensor, and from there the data are written into, and/or read out of, the data memory, or whether the storing and/or read-out of the data is accomplished from the superordinated unit.

The connection of the pH-sensor interface to the superordinated system can occur directly, or by means of a connecting cable.

In a presently preferred embodiment, the interface of the pH-sensor is a contactless interface, as is described in the European Patent Application No. 1 216 079 of the same assignee, now U.S. Pat. No. 6,705,898. The term "contactless" denotes that the interface on the sensor side is electrically, respectively galvanically, isolated from the interface on the transmitter side. The contactless interface can be, for example, an optical, capacitive, or inductive interface, with an inductive interface being presently preferred. For details concerning the structure of the interface, see the European Patent Application No. 1 216 079, which is here fully incorporated by reference.

Naturally, an interface with electrically conductive contacts can also be used for the implementation of the pH-sensor of the invention.

In a preferred embodiment, the pH-sensor of the invention has an analog-digital converter, which generates a digital signal as a function of the pH-value-dependent potential of the elementary sensor.

In addition, the pH-sensor of the invention preferably includes a microprocessor, which, on the one hand, controls the transfer of data between the interface of the pH-sensor and the superordinated system, and, on the other hand, controls the reading- and writing-processes of the digital data memory. It is especially preferred when the analog-digital converter is integrated into the microprocessor.

Preferably, the pH-sensor has a housing, into which the data memory, the interface, and, if necessary, further electronic components, such as the analog-digital converter and the microprocessor, are integrated.

For simple embodiments of the present invention, especially for those with electrically conductive transfer of the pH-value-dependent potential to the transmitter, it is possible to do without a microprocessor at the pH-sensor. The reading and/or writing of data from, respectively to, the digital data memory can in this case be controlled by the superordinated system, respectively, transmitter.

The digital data memory is preferably a multiply and/or a one-time writable memory unit. Presently, EEPROMs are especially preferred, with EPROMs being also basically suitable.

The digital data memory can especially store one or more of the following data:
Calibration data;
the sensitivity of the sensor determined at a first temperature, especially 25° C.;
the asymmetry potential determined at 25° C.;
the temperature offset;
logistical information, for example a SAP-code and/or an order number; the serial number;
the temperature range of application;
the pH range of application;
the extreme values of the operating temperature;
the extreme values of the operating pH;
the identification of a technician (for traceability of the calibration);
the service life;
the isothermal point of intersection,
the Sensor Check System status;
the pH measured value; and
the temperature measured value.

The superordinated unit, respectively transmitter, can preferably access all of the stored data by means of a read-command.

Preferably the superordinated unit, respectively transmitter, can, by means of write-commands, store one or more of the following data in the memory:
Calibration data;
the steepness of the potential determined at a first temperature, especially 25° C.;
the zero-point of the potential determined at 25° C.; the temperature offset;
the identification of a technician (for traceability of the calibration); and
the isothermal point of intersection.

At a first inspection of the sensor, the following data is written to the data memory by means of write-commands:
Logistical information;
temperature range of application; and
pH range of application.

The pH-sensor of the invention has the advantage that sensor-specific data, i.e. device data, process data, and/or historical data, are connected inseparably with the sensor. This enables, on the one hand, a pre-calibration of the sensor before it is installed at the site of application, and on the other hand, the use of a sensor at different transmitters, without a new calibration being imperative.

BRIEF DESCRIPTION OF THE DRAWINGS

Further aspects of the invention will become apparent from the dependent claims, the description of the examples of embodiments, and the drawings, which show as follows:

DESCRIPTION OF THE PREFERRED EMBODIMENTS

Figure 1:
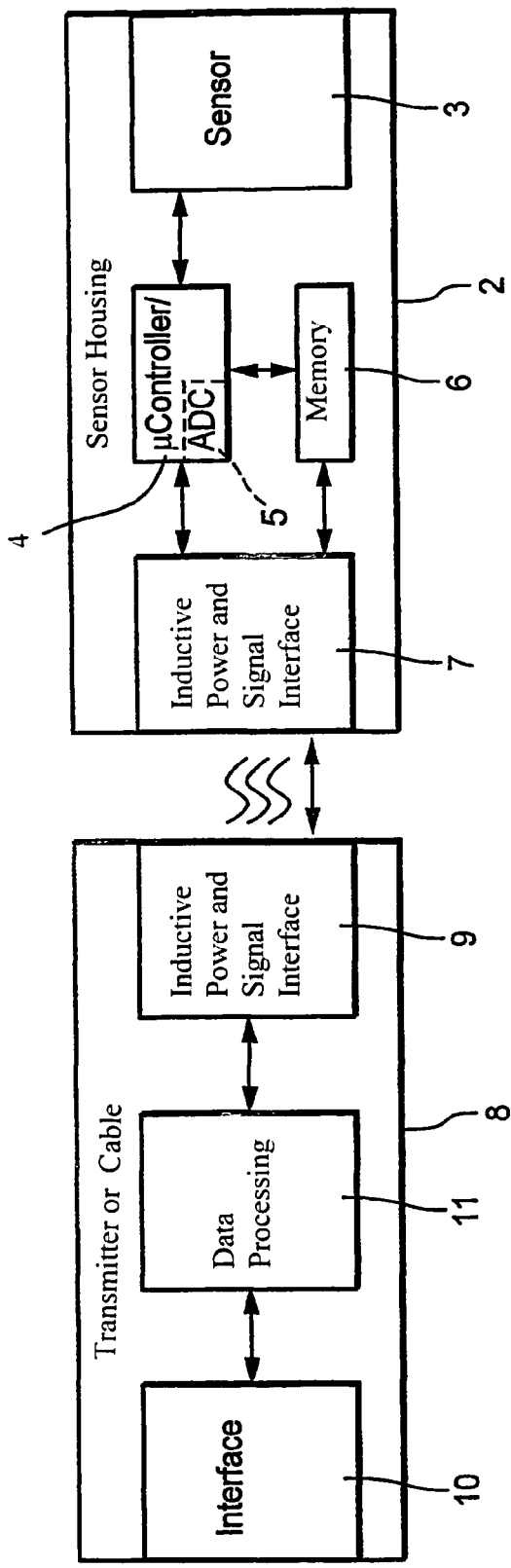
FIG. 1 a block diagram of a pH sensor of the invention.

An example of an embodiment of the invention will now be explained on the basis of FIGS. 1 and 2. The block diagram in FIG. 1 shows the components arranged in a sensor housing 2 of the pH-sensor 1, with the housing 2 being connected permanently, that is, inseparably, with an elementary sensor 3. The pH-sensor can be especially a rod-shaped pH-electrode, on whose end far from the medium the housing 2 is arranged.

In the housing 2, a microprocessor 4 is arranged, which preferably has an integrated analog-digital-converter (ADC) 5.

The microprocessor 4 is, on the one hand, coupled with the analog outputs of elementary sensor 3. On the other hand, the microprocessor is connected with a digital memory 6, which is an EEPROM in this embodiment. Lastly, the microprocessor 4 is connected with an inductive interface 7, by way of which, on the one hand, the power supply of the pH-sensor 1 is accomplished, and, on the other hand, the data transfer to and from a superordinated unit is accomplished, which, in this case, includes a transmitter 8. Optionally, a direct connection between the memory 6 and the interface 7 can also be provided.

The transmitter 8 includes a transmitter-side, inductive interface 9 for the energy supply of the pH-sensor 1, and for the digital data exchange with the pH-sensor. In addition, the transmitter includes a data processing unit 11, which is coupled with the transmitter-side inductive interface 9, and with a system-side interface 10. At the system-side interface, measurement data can be issued, and device-specific data exchanged. For this, all prevalent protocols, for example HART, Fieldbus, or Profibus, can be considered.

In measuring operation, the microprocessor 4 receives from the elementary sensor at least one analog signal, namely a pH-value-dependent potential and preferably also a temperature-dependent potential. The analog signals are converted by the ADC 5 into digital signals, which, on the one hand, are stored in the data memory 6, and on the other hand, can be issued to the transmitter 8 by way of the inductive interface 7.

For details of the inductive data transfer and power supply, see again U.S. Pat. No. 6,705,898.

The parameters for evaluating the pH-dependent potentials and, if necessary, the temperature data, are stored in the data memory 6 in the form of calibration data. The calibration data are issued, based on a read-command of the transmitter 8, either by way of the microprocessor 4, or directly, to the inductive interface 7, in order to make such available to the data processing unit 11 of the transmitter 8 for further processing, such as error compensation, etc. At the first calibration or at a recalibration of the pH-sensor 1, transmitter-side write-commands are issued for storing the determined calibration data, whereupon the data are stored in the EEPROM 6.

Figure 2:
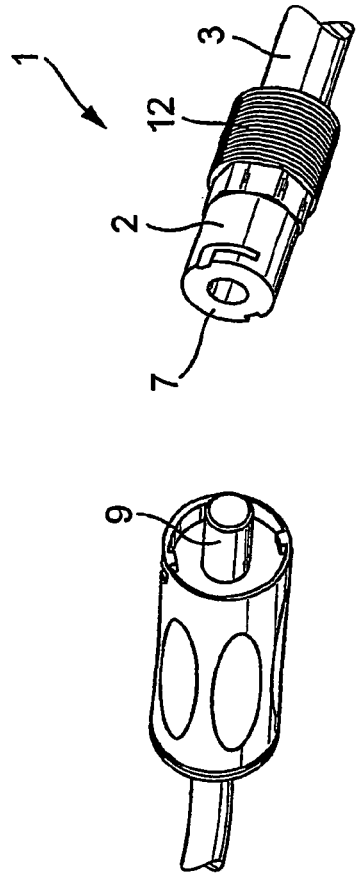
FIG. 2 a perspective detail view of the pH-sensor of the invention.

FIG. 2 shows an example of an embodiment for the mechanical arrangement of the housing 2 of the pH-sensor 1 on a rod-shaped elementary sensor 3, particularly a glass electrode.

The housing 2 has, on its lateral wall, threads 12, with which the pH-sensor 1 can be mounted in an assembly. The housing 2 has, facing away from the elementary sensor 3, a cylindrical end-section, in whose lateral wall the openings of a bayonet coupling are arranged. The inductive interface 7 is arranged in this end section. On its end, the housing 2 has a cylindrical, axial, blind hole, which serves as a receptacle for a housed ferrite core of a transmitter-side, inductive interface 9. In the example of the embodiment, the transmitter-side, inductive interface 9 is implemented as a plug on a cable which is connected with the transmitter. Equally as well, the transmitter-side interface 9 can be constructed directly on a transmitter housing, or similarly. On its end facing the pH-sensor 1, the plug has a sleeve-like, lateral wall, which protrudes axially, and coaxially surrounds the ferrite core. The sleeve-like, lateral wall encloses at least one part of the cylindrical end-section of the housing 2 when the plug is attached to the housing 2. Radially inwardly-projecting protrusions on the sleeve-like, lateral wall then engage with the openings of the bayonet coupling in order to secure the plug.

The invention claimed is:

1. A potentiometric sensor connectable to a superordinated unit, comprising:
   an elementary sensor for registering a potentiometric parameter, representative of pH and temperature values;
   an interface for issuing a potentiometric-parameter-dependent signal to the superordinated unit;
   a digital data memory, permanently connected with said elementary sensor,
   an analog-digital-converter for converting an analog signal issued from said elementary sensor into a digital signal, and
   a microprocessor for control of said digital data memory and/or control of said interface for communication with said superordinated unit, wherein:
   the potentiometric sensor is a pH sensor, and said elementary sensor comprises a pH-electrode and a temperature sensor therein;
   said digital memory stores one or more of the following items or information; the calibration data of said elementary sensor; the sensitivity of said elementary sensor determined at a first temperature, especially 25° C.; the asymmetry potential determined at 25° C.; the temperature offset; logistical information; the serial number of said elementary sensor; the temperature range of application; the pH range of application; the extreme values of the operating temperature; the extreme values of the operating pH; the identification of a technician; the service life; the isothermal point of intersection; and
   said data memory further stores historical data over a moving time-interval of sensor operation, and/or event-dependent historical data.

2. The potentiometric sensor as claimed in claim 1, wherein:
   said digital data memory is connected such that it can be controlled via said interface from the superordinated unit.

3. The potentiometric sensor as claimed in claim 1, wherein:
   the superordinated unit has a housing, and
   the potentiometric sensor is detachably connected with the housing of the superordinated unit via a mechanical coupling, which includes said interface.

4. The potentiometric sensor as claimed in claim 1, wherein:
   the superordinated unit has a cable, and
   the potentiometric sensor is detachably connected with the cable which communicates with the superordinated unit by means of a coupling which includes said interface.

5. The potentiometric sensor as claimed in claim 1, wherein:
   said interface, in addition to data communication, also ensures the power supply of the potentiometric sensor.

6. The potentiometric sensor as claimed in claim 1, wherein:
   said inter-face is an inductively coupled interface.

7. The potentiometric sensor as claimed in claim 1, wherein:
   said interface is an interface having galvanic contacts.

* * * * *